United States Patent
Yao et al.

(10) Patent No.: US 8,926,513 B2
(45) Date of Patent: Jan. 6, 2015

(54) ULTRASONIC DIAGNOSTIC APPARATUS, POSITIONAL INFORMATION ACQUIRING METHOD, AND COMPUTER PROGRAM PRODUCT

(75) Inventors: Cong Yao, Otawara (JP); Naohisa Kamiyama, Otawara (JP); Yoko Okamura, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 861 days.

(21) Appl. No.: 12/688,259

(22) Filed: Jan. 15, 2010

(65) Prior Publication Data

US 2010/0185092 A1    Jul. 22, 2010

(30) Foreign Application Priority Data

Jan. 20, 2009    (JP) ................................. 2009-010246

(51) Int. Cl.
*A61B 8/00* (2006.01)
*G06K 9/00* (2006.01)
*G06K 9/34* (2006.01)
*G06K 9/40* (2006.01)
*A61B 8/08* (2006.01)

(52) U.S. Cl.
CPC .................................... *A61B 8/0825* (2013.01)
USPC ........... 600/443; 600/438; 382/128; 382/173; 382/254

(58) Field of Classification Search
USPC .......... 600/437, 438, 443; 382/128, 168, 171, 382/172, 173, 266, 254
See application file for complete search history.

(56) References Cited

U.S. PATENT DOCUMENTS

| 6,500,118 | B1* | 12/2002 | Hashimoto | 600/437 |
| 7,949,171 | B2* | 5/2011 | Qing et al. | 382/131 |
| 2007/0239006 | A1* | 10/2007 | Kamiyama et al. | 600/437 |
| 2010/0099987 | A1* | 4/2010 | Sasaki et al. | 600/443 |

FOREIGN PATENT DOCUMENTS

| CN | 101032411 A | 9/2007 |
| JP | 2005-74225 | 3/2005 |
| JP | 2005-152346 | 6/2005 |
| JP | 2006-246974 | 9/2006 |
| JP | 2007-244575 | 9/2007 |
| JP | 2008-12141 | 1/2008 |

OTHER PUBLICATIONS

B. Brendel, et al., "Registration of 3D CT and Ultrasound Datasets of the Spine using Bone Structures", Computer Aided Surgery, vol. 7., 2002, pp. 146-155.

(Continued)

*Primary Examiner* — Katherine Fernandez
(74) *Attorney, Agent, or Firm* — Oblon, Spivak, McClelland, Maier & Neustadt, L.L.P.

(57) ABSTRACT

The analysis image generating unit generates section images from volume analysis data that is collected by sending an ultrasound wave down to a region under the ribs. The right/left identifying unit identifies the right or left breast from cyclic motion components in the section images. The extending direction detecting unit analyzes plane-A images or plane-B images generated from the same volume analysis data, or a plane-C thickness-added MIP image, and detects the rib extending direction. The extending direction detecting unit also determines the position of the ultrasound probe based on the relative displacement of the extending direction. The body mark generating unit generates a body mark from the analysis results obtained by the right/left identifying unit and the extending direction detecting unit. The image synthesizing unit integrates the display image generated by the display image generating unit and the body mark, and displays it on the monitor.

7 Claims, 12 Drawing Sheets

(56) References Cited

OTHER PUBLICATIONS

Yusuke Miyauchi, et al., "Probe Position Detecting System for Breast Cancer Screening Using Color Sensor", Jpn J Med Ultrasonics, vol. 35 Supplement, 2002, 2 pages (with Partial English Translation).

Chinese Office Action issued Sep. 7, 2011, in Patent Application No. 201010003804.9.

* cited by examiner

PROBE POSITION MARK

LEFT BREAST BODY MARK

PROBE POSITION MARK

RIGHT BREAST BODY MARK

LINE SEGMENT OF INTEREST 1

LINE SEGMENT OF INTEREST 2

LINE SEGMENT OF INTEREST 3
→ RIB EXTENDING DIRECTION

WHEN SETTING CENTER POINT IN INTERCOSTAL TISSUES

DETERMINE ULTRASOUND PROBE POSITION BASED ON INITIAL POSITION

ROTATE PROBE POSITION MARK IN
CHRONOLOGICAL ORDER FROM INITIAL POSITION

RIB EXTENDING DIRECTION, CURVATURE OF EXTENDING DIRECTION, AND DISTANCES BETWEEN RIB BONES

SKELETAL INFORMATION OF HEALTHY BODY

DETERMINE POSITION OF ULTRASOUND PROBE

GENERATE PANORAMIC IMAGE IN ACCORDANCE WITH
RELATIVE CHANGE OF RIB EXTENDING DIRECTION

ULTRASONIC DIAGNOSTIC APPARATUS, POSITIONAL INFORMATION ACQUIRING METHOD, AND COMPUTER PROGRAM PRODUCT

CROSS-REFERENCE TO RELATED APPLICATIONS

This application is based upon and claims the benefit of priority from the prior Japanese Patent Application No. 2009-10246, filed on Jan. 20, 2009; the entire contents of which are incorporated herein by reference.

BACKGROUND OF THE INVENTION

1. Field of the Invention

The present invention is related to an ultrasonic diagnostic apparatus, a positional information acquiring method, and a computer program product.

2. Description of the Related Art

Among conventional technologies, an ultrasonic diagnostic apparatus is advantageous in its operational ease and non-invasiveness without the possibility of exposure to radiation, to other medical diagnostic imaging devices such as an x-ray diagnostic device and an x-ray computer tomograph. The ultrasonic diagnostic apparatus is therefore widely used in examination and diagnosis of various parts of body tissues such as heart, liver, kidney, mammary gland, and muscles in today's medicine.

The ultrasonic diagnostic apparatus transmits an ultrasonic wave to a subject from an ultrasound probe, and generates an ultrasonic image based on the reflection wave of the ultrasonic wave reflected from the inner tissues of the subject.

In recent examinations incorporating an ultrasonic diagnostic apparatus such as ultrasonic breast examinations that are recommended for early detection of breast cancer, an ultrasound probe needs to be moved and rolled on the breast surface by a doctor or a clinical laboratory technician to find an optimal position for observation of a lesion. Thus, for the doctor to recognize the position of the lesion indicated in an ultrasonic image, it is important to obtain positional information of the ultrasound probe at the time of generating the ultrasonic image.

To obtain the positional information of the ultrasound probe, an ultrasonic diagnostic apparatus has been developed, in which a magnetic field generation coil that generates a magnetic signal is attached to a bed on which a subject lies and the ultrasound probe is provided with a magnetic sensor (see JP-A 2006-246974 (KOKAI) and JP-A 2007-244575 (KOKAI), for example). In such an ultrasonic diagnostic apparatus, the magnetic sensor that detects the magnetic signal generated by the magnetic field generation coil calculates coordinates of the position of the magnetic sensor with respect to the magnetic field generation coil so that the positional information of the ultrasound probe can be obtained.

Furthermore, an ultrasonic diagnostic apparatus in which the ultrasound probe is provided with an optical sensor has also been developed to obtain the positional information of the ultrasound probe (see, for example, "Development of System for Detecting Position of Breast Examination Probe Incorporating Color Sensor", The 81st Annual Scientific Meeting of the Japan Society of Ultrasonics in Medicine, S283, May, 2008). In such an ultrasonic diagnostic apparatus, the optical sensor reads a color pattern fixed onto the area of the subject that is to be examined so that the positional information of the ultrasound probe can be obtained.

The positional information of the ultrasound probe obtained in this manner is displayed, for example, as a body mark on the monitor together with an ultrasonic image so that the doctor who conducts an image diagnosis easily recognizes the position of the examination region in the ultrasonic image that is being viewed. A body mark is a brief description that roughly indicates the position and orientation of the ultrasound probe that is placed on the subject at the time of generating an ultrasonic image.

According to the above conventional technologies, however, the positional information of the ultrasound probe cannot be easily acquired. More specifically, with the above conventional technologies, because a positional sensor such as a magnetic sensor and an optical sensor needs to be additionally arranged in the ultrasound probe, the structure of the ultrasonic diagnostic apparatus becomes complicated, which increases the cost of production.

SUMMARY OF THE INVENTION

According to an aspect of the present invention, an ultrasonic diagnostic apparatus includes an ultrasound wave control unit that performs control in such a manner that a depth of an ultrasonic wave emitted from an ultrasound probe is set to a value deeper than an observation region of a subject; an image generating unit that generates a plurality of ultrasonic images in chronological order based on a reflection wave of the ultrasonic wave emitted by the ultrasound probe in accordance with the control performed by the ultrasound wave control unit; a positional information acquiring unit that acquires motion information from the ultrasonic images generated by the image generating unit in chronological order, identifies a left organ or a right organ that is being scanned by the ultrasound probe based on an intensity ratio of heartbeat-related motion components and respiration-related motion components in the motion information that is acquired, and acquires an identification result as positional information; and a display control unit that performs control in such a manner than the positional information acquired by the positional information acquiring unit on a predetermined displaying unit.

According to another aspect of the present invention, an ultrasonic diagnostic apparatus includes an ultrasound wave control unit that performs control in such a manner that a depth of an ultrasonic wave emitted from an ultrasound probe is set to a value deeper than an observation region of a subject and that three-dimensional scanning is conducted with the ultrasonic wave; an image generating unit that generates three-dimensional ultrasonic images based on a reflection wave of the ultrasound wave emitted by the ultrasound probe in accordance with the control performed by the ultrasound wave control unit; a positional information acquiring unit that detects through image analysis a rib extending direction depicted in the three-dimensional ultrasonic images generated by the image generating unit, and acquires the rib extending direction that is detected, as positional information of the ultrasound probe; and a display control unit that performs control in such a manner that the positional information acquired by the positional information acquiring unit is displayed on a predetermined displaying unit.

According to still another aspect of the present invention, a positional information acquiring method includes performing control by an ultrasound wave control unit in such a manner that a depth of an ultrasound wave emitted by an ultrasound probe is set to a value deeper than an observation region of a subject; generating ultrasonic images in chronological order by an image generating unit based on a reflection wave of the ultrasound wave emitted by the ultrasound probe in accordance with the control of the ultrasound wave control unit; acquiring motion information from the ultrasonic images generated by the image generating unit in chronological order, identifying a left organ or a right organ that is being scanned by the ultrasound probe based on an intensity ratio of heartbeat-related motion components and respiration-related motion components in the motion information that is acquired, and acquiring an identification result as positional information by a positional information acquiring unit; and performing control by a display control unit in such a manner that the positional information acquired by the positional information acquiring unit is displayed on a predetermined displaying unit.

According to still another aspect of the present invention, a positional information acquiring method includes performing control by an ultrasound wave control unit in such a manner that a depth of an ultrasound wave emitted by an ultrasound probe is set to a value deeper than an observation region of a subject and that three-dimensional scanning is conducted with the ultrasound wave; generating three-dimensional ultrasonic images by an image generating unit, based on a reflection wave of the ultrasound wave emitted by the ultrasound probe in accordance with the control performed by the ultrasound wave control unit; detecting, through image analysis, a rib extending direction depicted in the three-dimensional ultrasonic images generated by the image generating unit, and acquiring the rib extending direction that is detected, as positional information of the ultrasound probe by a positional information acquiring unit; and performing control by a display control unit in such a manner that the positional information acquired by the positional information acquiring unit is displayed on a predetermined displaying unit.

According to still another aspect of the present invention, a computer program product having a computer readable recording medium including a plurality of computer executable instructions to execute image processing, wherein the instructions cause a computer to: performing control in such a manner that a depth of an ultrasound wave emitted by an ultrasound probe is set to a value deeper than an observation region of a subject; generating a plurality of ultrasonic images in chronological order based on a reflection wave of the ultrasound wave emitted by the ultrasound probe; acquiring motion information from the ultrasonic images generated in chronological order, identifying a left organ or a right organ that is being scanned by the ultrasound probe based on an intensity ratio of heartbeat-related motion components and respiration-related motion components in the motion information that is acquired, and acquiring an identification result as positional information; and performing control in such a manner that the positional information that is acquired is displayed on a predetermined displaying unit.

According to still another aspect of the present invention, a computer program product having a computer readable recording medium including a plurality of computer executable instructions to execute image processing, wherein the instructions cause a computer to: performing control in such a manner that a depth of an ultrasound wave emitted by an ultrasound probe is set to a value deeper than an observation region of a subject and that three-dimensional scanning is conducted with the ultrasound wave; generating three-dimensional ultrasonic images based on a reflection wave of the ultrasound wave emitted by the ultrasound probe; detecting, through image analysis, a rib extending direction depicted in the three-dimensional ultrasonic images that are generated, and acquiring the rib extending direction that is detected, as positional information of the ultrasound probe; and performing control in such a manner that the positional information that is acquired is displayed on a predetermined displaying unit.

DETAILED DESCRIPTION OF THE PREFERRED EMBODIMENTS

Figure 1:
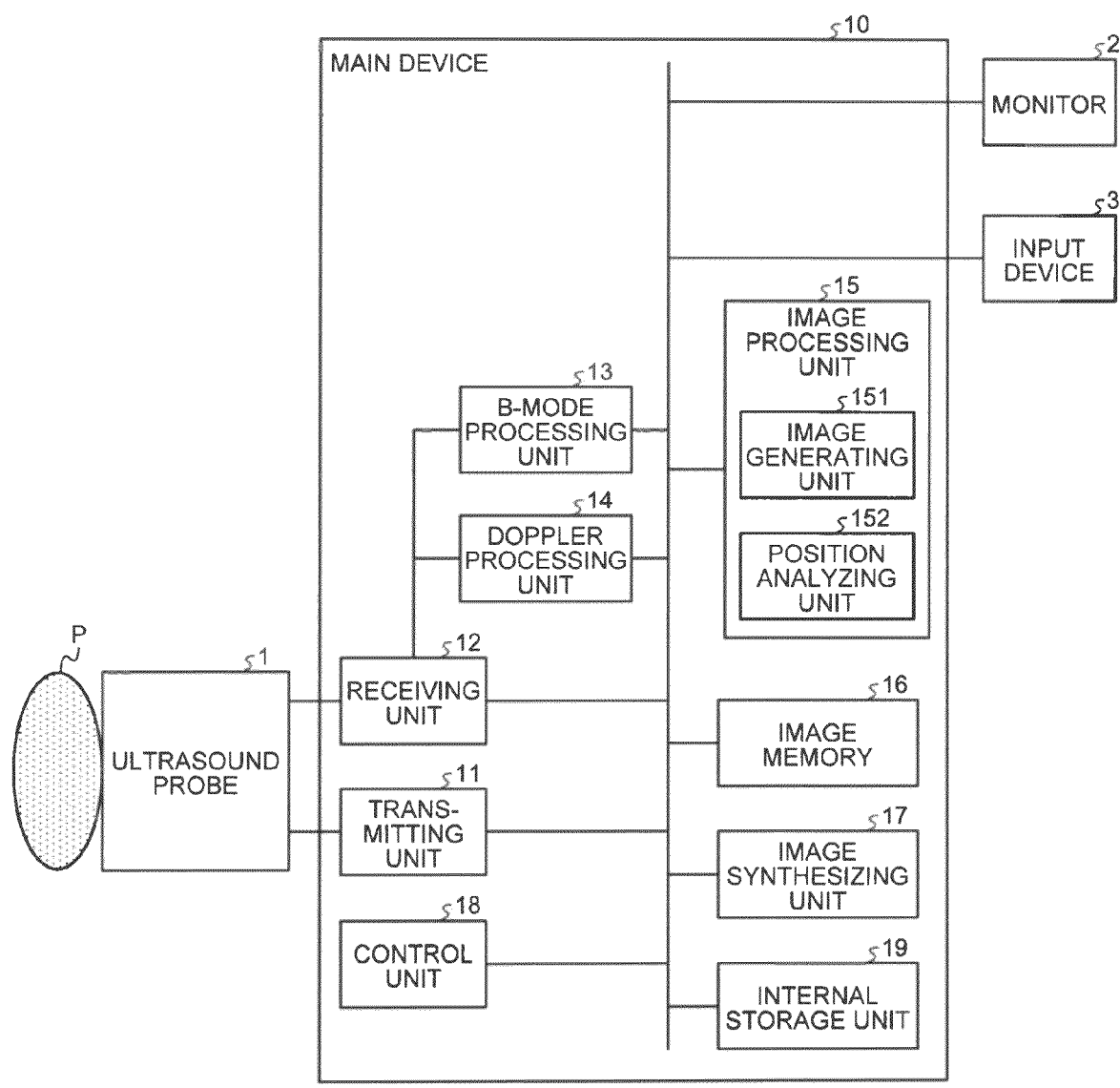
FIG. 1 is a diagram for explaining a configuration of an ultrasonic diagnostic apparatus according to the present embodiment.

Exemplary embodiments of an ultrasonic diagnostic apparatus, a positional information acquiring method, and a computer program product according to the present invention are explained in detail below with reference to the First, a configuration of an ultrasonic diagnostic apparatus according to the present embodiment is explained. FIG. 1 is a diagram for explaining a configuration of an ultrasonic diagnostic apparatus according to the present embodiment. As shown in FIG. 1, the ultrasonic diagnostic apparatus according to the present embodiment includes an ultrasound probe 1, a monitor 2, an input device 3, and a main device 10.

The ultrasound probe 1 includes an array of piezoelectric oscillators. These piezoelectric oscillators generate an ultrasound wave in accordance with a drive signal supplied from a transmitting unit 11 of the main device 10, which is described later, and also receives a wave reflected from a subject P and converts it to an electronic signal. The ultrasound probe 1 includes a matching layer provided on the piezoelectric oscillators, a backing material that prevents an ultrasound wave from propagating from the piezoelectric oscillators to the rear, and the like.

When an ultrasound wave is emitted from the ultrasound probe 1 to the subject P, the emitted ultrasound wave is reflected from the discontinuous planes of acoustic impedances in the body tissue of the subject P, and is received as a reflection wave signal by the piezoelectric oscillators of the ultrasound probe 1. The amplitude of the received reflection wave signal depends on a difference in the acoustic impedances produced at the discontinuous planes from which the ultrasound wave is reflected. When the emitted ultrasonic pulses are reflected on the surface of the moving blood stream or cardiac wall, the reflection wave signals undergo a frequency shift due to the Doppler effect, in accordance with the velocity components of the ultrasound wave transmission direction in the moving object.

The ultrasound probe 1 according to the present embodiment includes an oscillation motor and an oscillation circuit that mechanically oscillate the piezoelectric oscillators, and the subject P can be three-dimensionally scanned by the oscillation of the piezoelectric oscillators. In other words, the operator can automatically obtain three-dimensional reflection wave data (volume data) of the subject P scanned consecutively on multiple sections simply, by touching the subject P with the ultrasound probe 1 according to the present embodiment. Further, when scanning the subject P in three dimensions, distances between the sections can be accurately detected on the basis of the controlled oscillation speed.

The present invention is applicable to a two-dimensional ultrasound probe, in which the piezoelectric oscillators are arranged two-dimensionally in a lattice pattern in the ultrasound probe 1. By use of the two-dimensional ultrasound probe, the ultrasonic diagnostic apparatus can obtain volume data substantially in the same length of time in principle as when obtaining the two-dimensional reflection wave data by a conventional one-dimensional probe.

The monitor 2 displays a graphical user interface (GUI) with which the operator of the ultrasonic diagnostic apparatus inputs various setting requests through the input device 3, and also displays an ultrasonic image generated by the main device 10.

The input device 3 includes a mouse, a keyboard, buttons, a panel switch, a touch command screen, a foot switch, a trackball, and the like. The input device 3 receives various setting requests input by the operator of the ultrasonic diagnostic apparatus, and sends the received setting requests (for example, a region-of-interest setting request) to the main device 10. For example, when the operator presses the "stop" button or the "freeze" button of the input device 3, the ultrasound wave transmission and reception is terminated, and the ultrasonic diagnostic apparatus is put into suspend mode.

The main device 10 generates an ultrasonic image in accordance with the reflected wave received by the ultrasound probe 1. As illustrated in FIG. 1, the main device 10 includes the transmitting unit 11, a receiving unit 12, a B-mode processing unit 13, a Doppler processing unit 14, an image processing unit 15, an image memory 16, an image synthesizing unit 17, a control unit 18, and an internal storage unit 19.

The transmitting unit 11 includes a trigger generating circuit, a delay circuit, a pulsar circuit, and the like, and supplies a drive signal to the ultrasound probe 1. The pulsar circuit repeatedly generates rate pulses at a predetermined rate frequency to form a transmission ultrasound wave. The delay circuit gives a delay time for each piezoelectric oscillator, which is necessary to concentrate the ultrasound wave emitted by the ultrasound probe 1 into a beam and thereby determine the transmission directional characters, to each rate pulse generated by the pulsar circuit. Furthermore, the trigger generating circuit applies a drive signal (drive pulses) to the ultrasound probe 1 at the timing based on the rate pulses.

The transmitting unit 11 has a function of quickly changing the transmission frequencies, the transmission drive voltages, and the like to execute a certain scan sequence, based on the later-described control performed by the control unit 18. The transmission drive voltages are changed by a linear-amplifier oscillation circuit that can instantaneously change the voltage values or a mechanism that can electrically switch among multiple power units.

The receiving unit 12 includes an amplifying circuit, an analog-digital (A/D) converter, an adder, and the like, and executes various processes on the reflection wave signal received by the ultrasound probe 1 to generate reflection wave data. The amplifying circuit amplifies the reflection wave signal and executes a gain correcting process thereon. The A/D converter performs an A/D conversion onto the gain-corrected reflection wave signal and gives the signal a delay time that is necessary to determine the reception directional characteristics. The adder performs addition onto the reflection wave signal processed by the A/D converter and thereby generates the reflection wave data. Through the addition performed by the adder, the reflection components in a direction corresponding to the reception directional characteristics of the reflection wave signal are emphasized. According to the present embodiment, the receiving unit 12 generates three-dimensional reflection wave data.

In this manner, the transmitting unit 11 controls the transmission directional characteristics in the transmission of the ultrasound wave, while the receiving unit 12 controls the reception directional characteristics in the reception of the ultrasound wave.

The B-mode processing unit 13 receives from the receiving unit 12 the reflection wave data, which is the processed reflection wave signal subjected to the gain correcting process, the A/D converting process, and the adding process, and performs logarithmic amplification and an envelope detecting process to generate data (B-mode data) that expresses the signal intensity in brightness. According to the present embodiment, the B-mode processing unit 13 generates three-dimensional B-mode data from the three-dimensional reflection wave data.

The Doppler processing unit 14 performs a frequency analysis on the speed information of the reflection wave data received from the receiving unit 12, extracts echo components of the blood stream, the tissue, and the contrast agent that are affected by the Doppler effect, and generates data (Doppler data) by extracting moving body information including the average speed, the dispersion, and the power for different points. According to the present embodiment, the Doppler processing unit 14 generates three-dimensional Doppler data from the three-dimensional reflection wave data.

The image processing unit 15 includes an image generating unit 151 that generates an ultrasonic image and a position analyzing unit 152 that analyzes the ultrasonic image generated by the image generating unit 151 and analyzes the positional information of the ultrasound probe 1 on the subject P at the time of generating the ultrasonic image.

As an ultrasonic image, the image generating unit 151 generates, from the B-mode data generated by the B-mode processing unit 13, a B-mode image that expresses the intensity of the reflected wave in brightness, and also generates, from the Doppler data generated by the Doppler processing unit 14, a Doppler image, which is an average speed image, a dispersion image, a power image, or a combination image thereof indicating the information of the moving body.

The image generating unit 151 generally performs a conversion (scan conversion) of a scan line signal string obtained by ultrasonic scanning into a video-format scan line signal string such as for television and thereby generates an ultrasonic image as a display image. In addition to the scan conversion, the image generating unit 151 performs various kinds of image processing by use of image frames after the scan conversion, such as image processing for reconfiguring an average brightness image (smoothing process) and image processing using a differentiation filter in the image (edge emphasizing process).

Moreover, when receiving the three-dimensional reflection wave data such as three-dimensional B-mode data and three-dimensional Doppler data, the image generating unit 151 performs volume rendering or the like by use of a three-dimensional reconfiguration algorithm to reconfigure the three-dimensional ultrasonic image.

The image generating process of the image generating unit 151 and the analyzing process of the position analyzing unit 152 will be described later.

The image memory 16 stores therein ultrasonic images generated by the image generating unit 151.

The image synthesizing unit 17 superimposes character information of various parameters, scales, body marks, and the like onto the ultrasonic image generated by the image generating unit 151 and outputs the image as a video signal to the monitor 2.

The control unit 18 controls the entire process of the ultrasonic diagnostic apparatus. More specifically, the control unit 18 controls the processes performed by the transmitting unit 11, the receiving unit 12, the B-mode processing unit 13, the Doppler processing unit 14, and the image processing unit 15, in accordance with the various setting requests input by the operator on the input device 3 and various control programs read from the internal storage unit 19. The control unit 18 also exercises control so that the ultrasonic image stored in the image memory 16 and the image produced by the image synthesizing unit 17 are displayed on the monitor 2.

The internal storage unit 19 stores therein control programs for the ultrasound wave transmission and reception, image processing, and display processing, and various kinds of data such as diagnostic information (e.g., patient IDs and doctor's remarks), diagnostic protocols, and various body marks. The internal storage unit 19 is also used as storage of the images stored in the image memory 16, if necessary. The data stored in the internal storage unit 19 may be transmitted to an external peripheral device by way of a not-shown interface circuit.

In this manner, the ultrasonic diagnostic apparatus according to the present embodiment generates an ultrasonic image based on the reflected wave of the ultrasound wave emitted from the ultrasound probe 1. The main feature of this embodiment resides in that the positional information of the ultrasound probe can be easily acquired at the time of generating the ultrasonic image by the following processes performed by the image generating unit 151 and the position analyzing unit 152.

Figure 2:
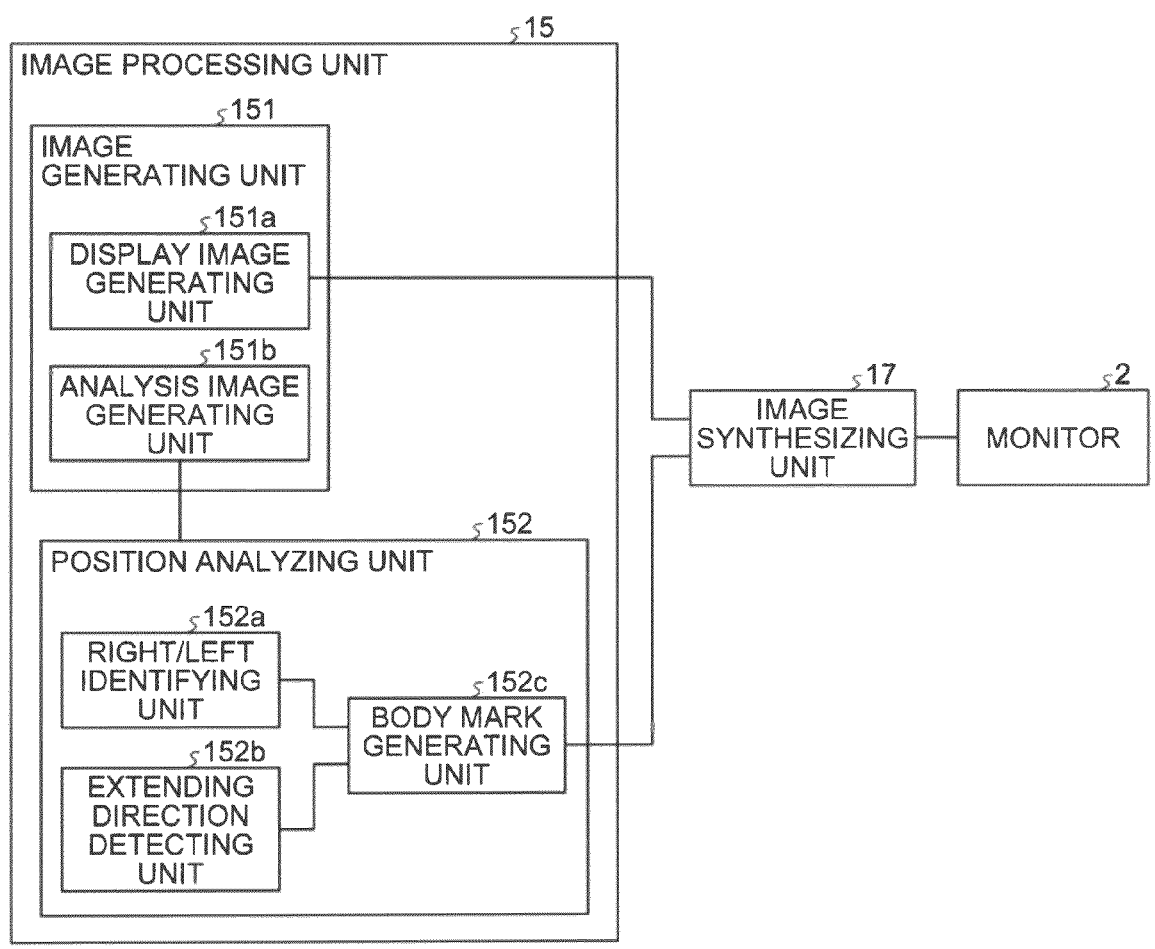
FIG. 2 is a diagram for explaining a configuration of an image processing unit according to the present embodiment.
Figure 3:
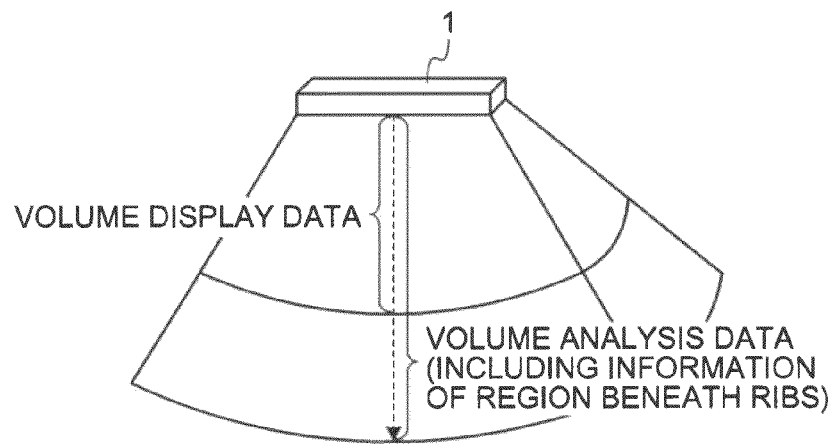
FIG. 3 is a diagram for explaining volume data according to the present embodiment.
Figure 4:
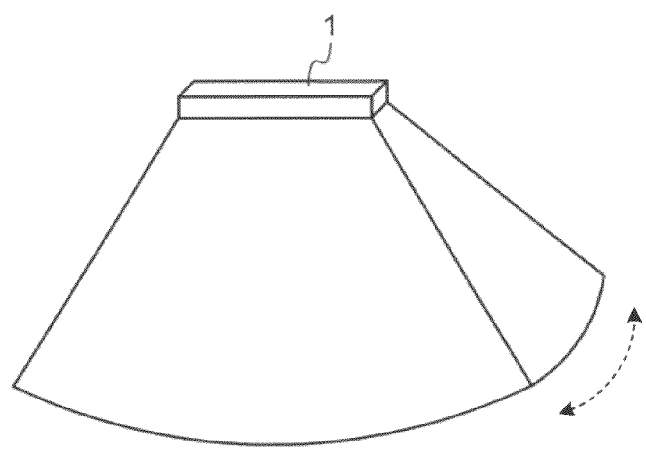
FIG. 4 is a diagram for explaining planes A, B, and C.
Figure 4:
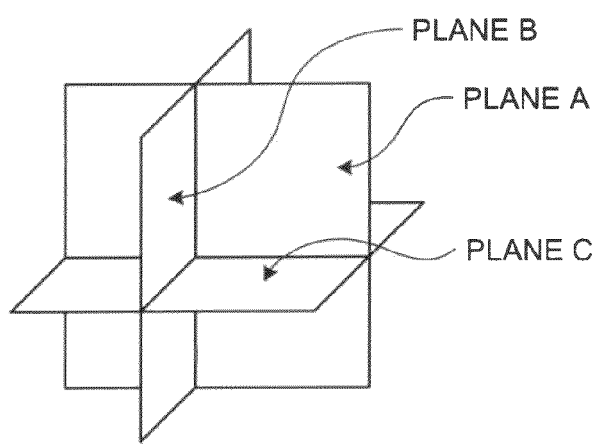
Figure 5A:
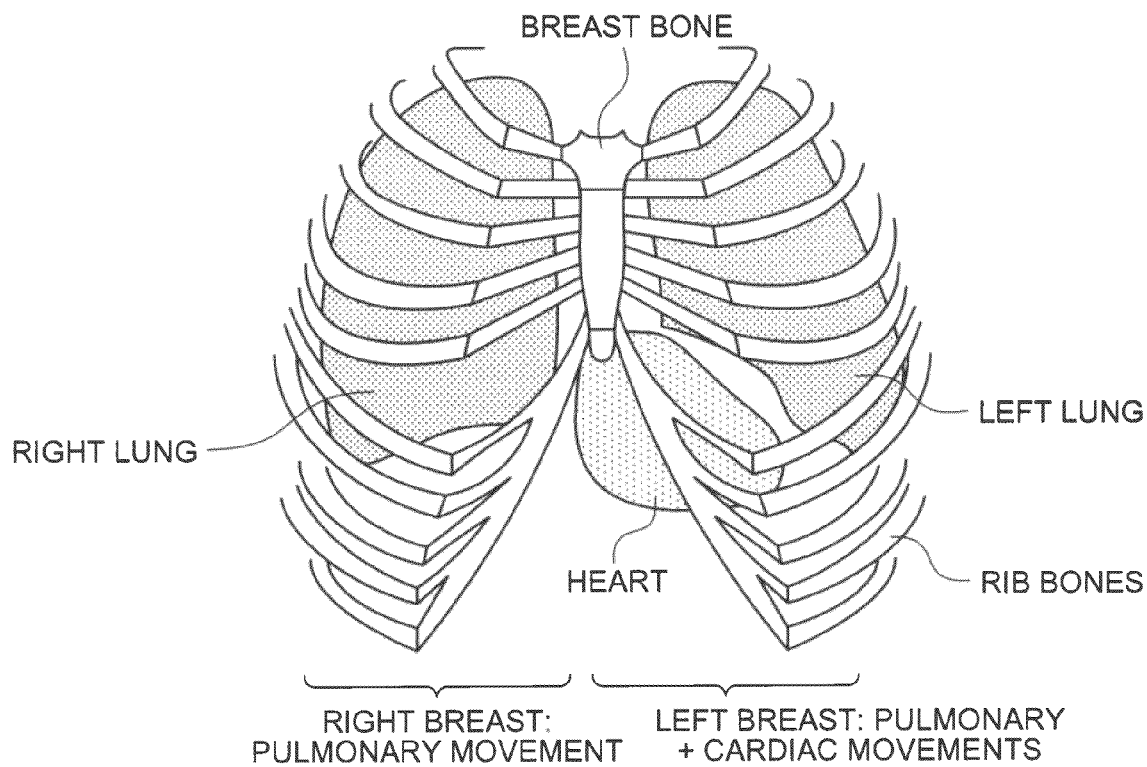
FIGS. 5A and 5B are diagrams for explaining a right/left identifying unit.
Figure 5B:
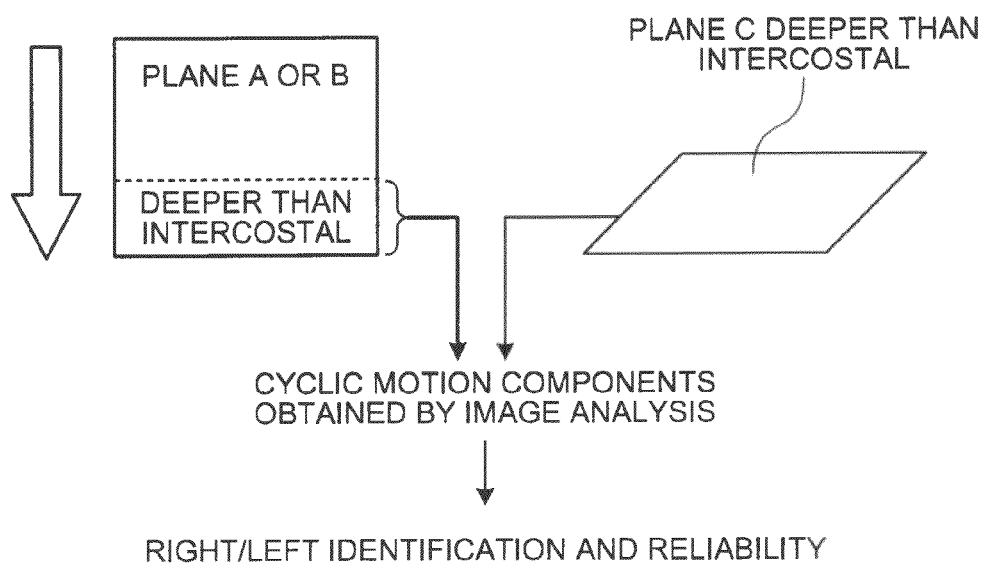
Figure 6:
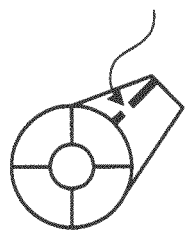
FIG. 6 is a diagram for explaining a process performed by a body mark generating unit by use of the processing results obtained by the right/left identifying unit.
Figure 6:
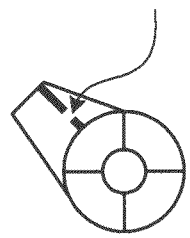
Figure 7A:
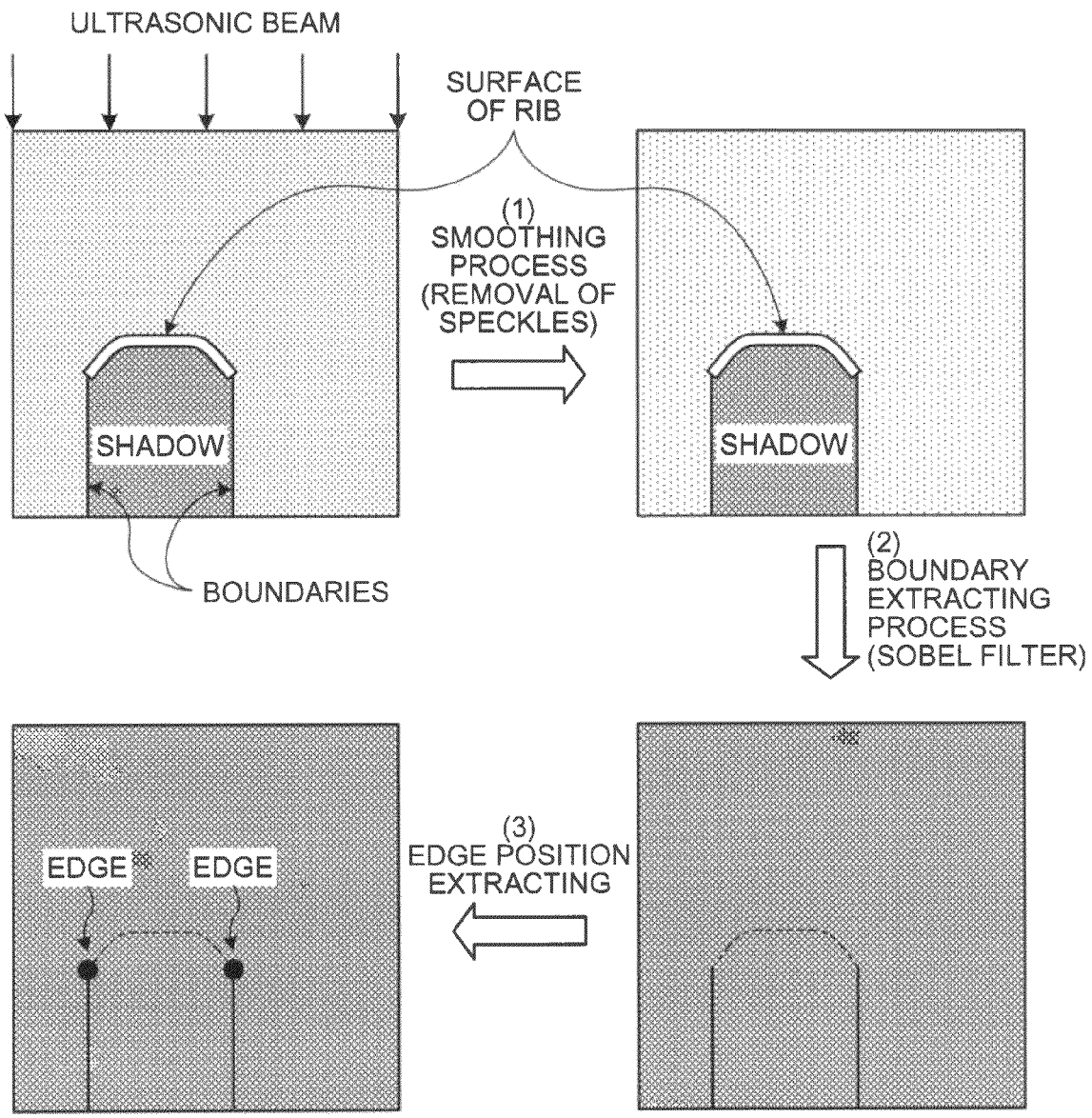
FIGS. 7A and 7B are diagrams for explaining the first method executed by an extending direction detecting unit.
Figure 7B:
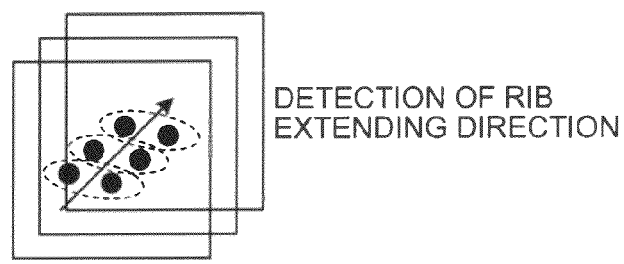
Figure 8:
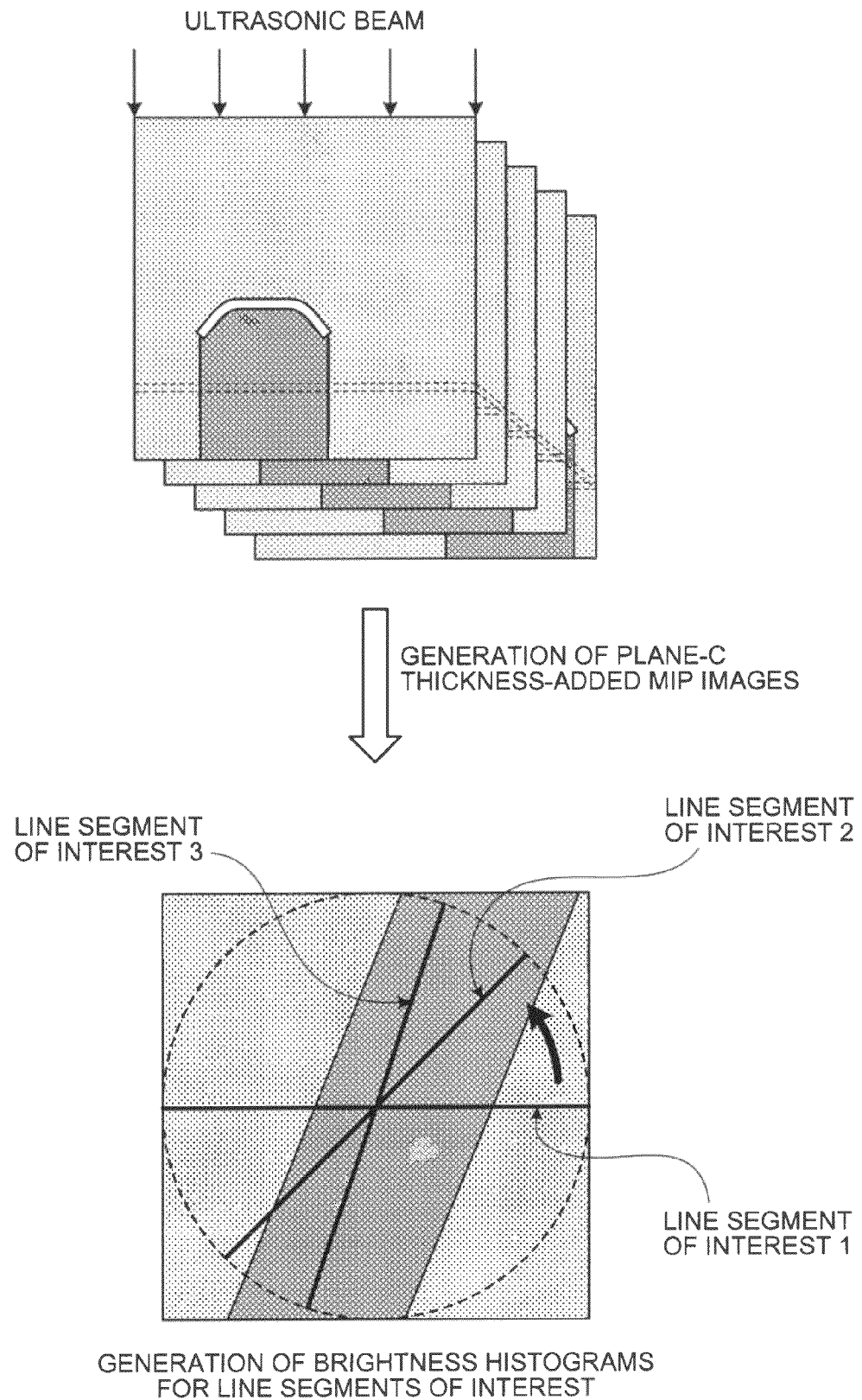
FIGS. 8, 9A, and 9B are diagrams for explaining the second method executed by the extending direction detecting unit.
Figure 9A:
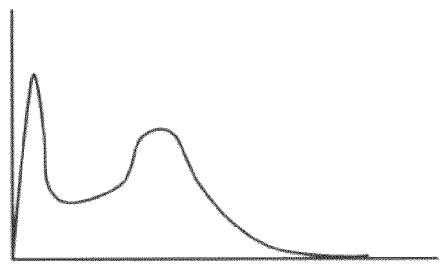
Figure 9A:
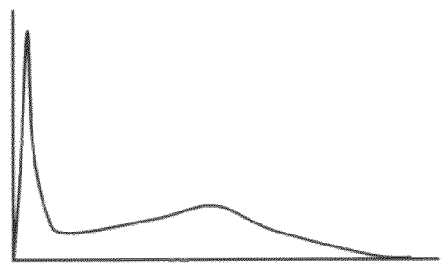
Figure 9A:
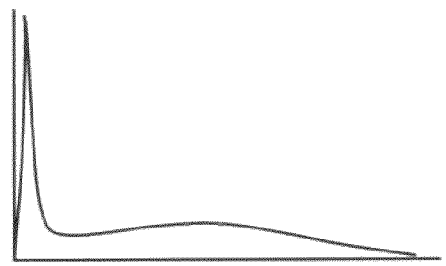
Figure 9B:
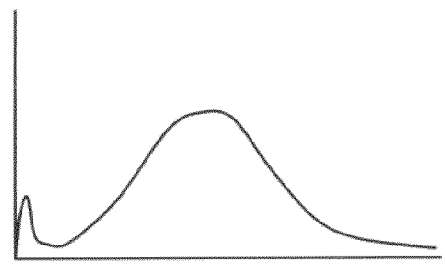
Figure 10A:
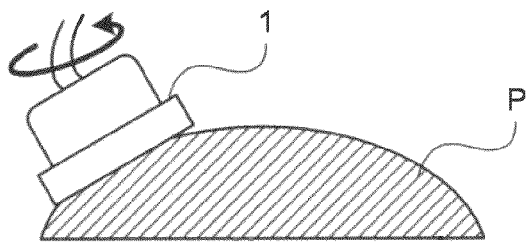
FIGS. 10A and 10B are diagrams for explaining the position detecting method executed for the ultrasound probe by the extending direction detecting unit.
Figure 10B:
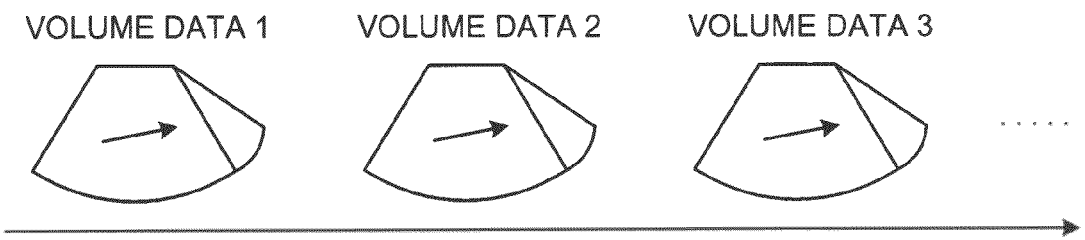
Figure 11:
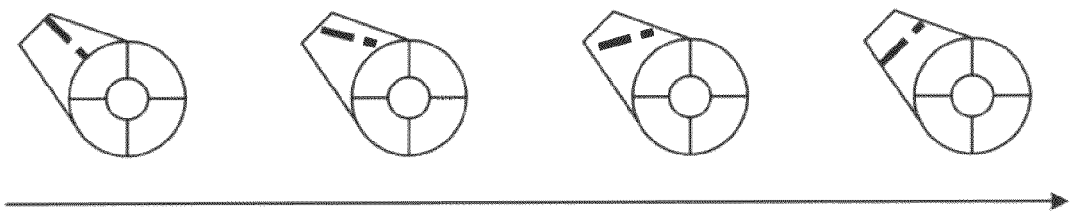
FIG. 11 is a diagram for explaining the process executed by the body mark generating unit by use of the processing results obtained by the extending direction detecting unit.

The processes performed by the image generating unit 151 and the position analyzing unit 152 are explained with reference to FIGS. 2 to 11. FIG. 2 is a diagram for explaining a configuration of an image processing unit according to the present embodiment, and FIG. 3 is a diagram for explaining the volume data according to the present embodiment. FIG. 4 is a diagram for explaining planes A, B, and C, and FIGS. 5A and 5B are diagrams for explaining the right/left identifying unit. FIG. 6 is a diagram for explaining the process performed by the body mark generating unit by use of the process result obtained by the right/left identifying unit, and FIGS. 7A and 7B are diagrams for explaining the first method executed by the extending direction detecting unit. FIGS. 8, 9A, and 9B are diagrams for explaining the second method executed by the extending direction detecting unit, and FIGS. 10A and 10B are diagrams for explaining the method of detecting the position of the ultrasound probe executed by the extending direction detecting unit. FIG. 11 is a diagram for explaining the process performed by the body mark generating unit by use of the process result obtained by the extending direction detecting unit.

In the following description, it is assumed that the ultrasound probe 1 three-dimensionally scans the breast of the subject P in an ultrasound breast examination to generate three-dimensional reflection wave data.

As illustrated in FIG. 2, the image generating unit 151 of the image processing unit 15 according to the present embodiment includes a display image generating unit 151a and an analysis image generating unit 151b. The position analyzing unit 152 of the image processing unit 15 according to the present embodiment includes a right/left identifying unit 152a, an extending direction detecting unit 152b, and a body mark generating unit 152c.

According to the present embodiment, to analyze the positional information of the ultrasound probe 1, the depth of the ultrasound wave emitted from the ultrasound probe 1 is automatically set by the control unit 18 deeper than the breast of the subject P who is to undergo the examination, or more specifically, deeper than the ribs of the subject P. For example, when the examination depth is 4 centimeters, the ultrasound probe 1 emits an ultrasound wave down to the depth of "7 centimeters", and the receiving unit 12 generates three-dimensional reflection wave data corresponding to the analysis depth of "7 centimeters".

Then, as illustrated in FIG. 3, the display image generating unit 151a uses the three-dimensional B-mode data generated from the three-dimensional reflection wave data of the examination depth as volume display data, and generates from this volume display data an ultrasonic display image (e.g., a volume rendering image and a section image) that is to be displayed on the monitor 2 for the doctor to conduct an image diagnosis.

Furthermore, as illustrated in FIG. 3, the analysis image generating unit 151b uses the three-dimensional B-mode data generated from the three-dimensional reflection wave data of different depths including information of a region deeper than the rib as volume analysis data, and generates from this volume analysis data an ultrasonic analysis image that is used by the position analyzing unit 152 to conduct an image analysis. More specifically, the analysis image generating unit 151b generates different section images as ultrasonic analysis images.

Three types of sectional surfaces (planes A, B, and C) along which section images are generated from a three-dimensional ultrasonic image in the ultrasonic diagnostic apparatus are now explained. First, as illustrated in FIG. 4, the plane A is a sectional surface of the mechanically oscillating ultrasound probe 1 defined by the alignment direction of the piezoelectric oscillators and the ultrasonic transmission direction. As illustrated in FIG. 4, the plane B is a sectional surface defined by the alignment direction of the piezoelectric oscillators and the oscillating direction. As illustrated in FIG. 4, the plane C is a sectional surface perpendicular to the ultrasonic transmission direction.

First, the analysis image generating unit 151b generates section images of planes A, B, and C from the volume analysis data that is generated successively in chronological order. It is assumed that the position of the ultrasound probe 1 at this point is fixed to the initial position on the breast of the subject P (for example, 45 degrees downward from the underarm of the subject P) by the operator.

Then, the right/left identifying unit 152a identifies the right or left breast that is being subjected to the scanning by the ultrasound probe 1, by use of the section images generated by the analysis image generating unit 151*b* in chronological order.

As illustrated in FIG. 5A, among the cyclic motions in the breast of the subject P, the left breast includes the pulmonary and cardiac motions, while the right breast includes the pulmonary motions only.

To identify whether the ultrasonic beam is scanning the left breast or the right breast, the right/left identifying unit 152*a* performs an image analysis on a certain region along the plane A or B at a certain position beneath the ribs, or on the plane C of a certain position beneath the ribs, in chronological order to acquire cyclic motion components, as illustrated in FIG. 5B. The right/left identifying unit 152*a* thereby identifies the right or left, and calculates the reliability of the identification result.

For example, the right/left identifying unit 152*a* extracts feature points from multiple plane-A images in chronological order, and obtains cyclic motion components of the feature points in chronological order. Then, the right/left identifying unit 152*a* makes an identification of the "left" when, among the obtained cyclic motion components, the ratio of the intensity of the motion components in a cycle of approximately 1 second (heartbeat-related motions) to the intensity of the motion components in a cycle of approximately 5 seconds (respiration-related motions) is greater than or equal to a certain percentage (e.g., 60%), while it makes an identification of the "right" when the ratio of the intensity of the motion components in a cycle of approximately 5 seconds (respiration-related motions) to the intensity of the motion components in a cycle of approximately 1 second (heartbeat-related motions) is greater than or equal to a certain percentage (e.g., 60%). Thereafter, the right/left identifying unit 152*a* calculates the reliability in accordance with, for example, the intensity ratio that is used in the identification.

Then, based on the identification result obtained by the right/left identifying unit 152*a*, the body mark generating unit 152*c* generates a body mark, for example, by combining the left or right breast body mark with the probe position mark that indicates the initial position of the ultrasound probe 1, as illustrated in FIG. 6. The body mark generating unit 152*c* obtains these body marks from the internal storage unit 19.

Then, the image synthesizing unit 17 generates a composite image by integrating the display image generated by the display image generating unit 151*a* and the body mark to which the probe position mark is attached by the body mark generating unit 152*c*. The monitor 2 displays the composite image generated by the image synthesizing unit 17, in accordance with the control of the control unit 18. In this manner, the display image to which the left or right body mark is attached is automatically presented to the operator, without having to manually input the body mark.

After the right/left identifying unit 152*a* identifies the right or left, the analysis image generating unit 151*b* generates an image that is used by the extending direction detecting unit 152*b* to detect the rib extending direction by the image processing. More specifically, the analysis image generating unit 151*b* generates different section images in accordance with an extending direction detecting method (the first or second method) executed by the extending direction detecting unit 152*b*.

First, the first method executed by the extending direction detecting unit 152*b* is explained. According to the first method, the analysis image generating unit 151*b* generates multiple plane-A images and/or multiple plane-B images by sectioning the volume analysis data generated at a time when the ultrasound probe 1 is placed at the initial position by multiple planes A and/or planes B. In the following explanation, the plane-A images generated by the analysis image generating unit 151*b* are described.

As illustrated in FIG. 7A, the reflection of the ultrasound wave on the rib surface is intense, which makes the brightness of the rib surface region high in a plane-A image that always contains the rib bone of the subject P. In contrast, the region under the rib surface is shown as a shadow with a low brightness in the plane-A image. Furthermore, in the plane-A image, the boundaries of the shadow are drawn in straight lines because they are parallel to the ultrasonic beams.

Thus, the extending direction detecting unit 152*b* first performs a smoothing process to remove speckles that appear in the rib surface and the intercostal region outside the shadow in the plane-A image (see (1) in FIG. 7A).

Next, the extending direction detecting unit 152*b* performs a boundary extracting process onto the plane-A image that has been subjected to the smoothing process, by use of the Sobel filter to detect the boundary of the rib region and the intercostal region (see (2) in FIG. 7A). The present invention is applicable to the extending direction detecting unit 152*b* that adopts the Hough transform instead of the Sobel filter in the boundary extracting process.

Thereafter, the extending direction detecting unit 152*b* extracts the position of the rib edges from the plane-A image that has been subjected to the Sobel filter processing (see (3) in FIG. 7A). In this manner, the extending direction detecting unit 152*b* extracts two edges of the rib bone, as illustrated in FIG. 7A. When the plane-A image contains two rib bones or more, the extending direction detecting unit 152*b* can distinguish the edges of each rib based on the distances between the edges.

The extending direction detecting unit 152*b* performs the above process on each of the plane-A images generated from the same volume analysis data, as illustrated in FIG. 7B. The extending direction detecting unit 152*b* detects the rib extending direction included in the volume analysis data, in accordance with the special continuity of a rib.

The first method is executable when using multiple plane-B images or when using multiple plane-A images and multiple plane-B images.

The second method executed by the extending direction detecting unit 152*b* is now explained. According to the second method, the analysis image generating unit 151*b* generates a thickness-added maximum intensity projection (MIP) image beneath the ribs in the plane C from the volume analysis data generated at a certain time when the ultrasound probe 1 is placed at the initial position, as illustrate in FIG. 8.

Because the thickness-added MIP image of the plane C includes information on the region beneath the ribs, the following feature is observed. The shadow portion under the rib surface (hereinafter, "rib shadow") has a low brightness in comparison with the projection region of the intercostal tissue. In the thickness-added MIP image of the plane C, the projected intercostal tissue regions and the rib shadows are alternately arranged, as illustrated in FIG. 8, and thus the extending directions of the ribs are described as stripes.

The extending direction detecting unit 152*b* that executes the second method determines, for example, a center point in the low-brightness region of the thickness-added MIP image of the plane C, and generates a brightness histogram of pixels on each of line segments of interest that pass the center. For example, as illustrated in FIG. 8, the extending direction detecting unit 152*b* turns the line segments of interest around the determined center point, and generates a histogram individually for the "line segment of interest 1, the line segment of interest 2, the line segment of interest 3, . . . ".

For example, the extending direction detecting unit 152b generates histograms for the line segments of interest 1, 2, and 3, as illustrated in FIG. 9A. Then, the extending direction detecting unit 152b analyzes the generated histograms of the line segments of interest to find the rib extending direction. For example, the extending direction detecting unit 152b determines the direction of the line segment of interest 3 in which the low brightness appears with the highest frequency in the histogram as the rib extending direction, as illustrated in FIG. 9A.

When the center point is defined in a high-brightness intercostal tissue region, the extending direction detecting unit 152b determines the line segment of interest in which the high brightness appears with the highest frequency as the rib extending direction, as illustrated in FIG. 9B.

The second method is executable if the region above the rib surface is included in the range for generating the thickness-added MIP image of the plane C, as long as the region beneath the ribs is included and the information on the rib shadow can be reflected. The second method is not limited to the use of line segments of interest, but may be used when analyzing the brightness values of all the pixels in the thickness-added MIP image of the plane C to determine the rib extending direction.

When the operator moves the ultrasound probe 1 on the breast of the subject P after the rib extending direction at the initial position is detected, as illustrated in FIG. 10A, to collect new volume data, the extending direction detecting unit 152b repeats the rib extending direction detecting process according to the first or second method.

For example, the extending direction detecting unit 152b detects the rib extending direction according to the first or second method, in volume data 1, 2, and 3, which is volume analysis data collected in chronological order after the rib extending direction at the initial position is detected, as illustrated in FIG. 10B, and determines the position of the ultrasound probe 1 from the initial position.

In other words, the extending direction detecting unit 152b calculates a relative change of the detected rib extending direction in the volume data 1 and the rib extending direction detected at the initial position, and acquires a relative displacement (rotation angle) with respect to the initial position of the ultrasound probe 1 to determine the position of the ultrasound probe 1 at the time of generating the volume data 1.

Similarly, the extending direction detecting unit 152b calculates a relative change of the rib extending direction detected in the volume data 2 and the rib extending direction detected in the volume data 1, and acquires a relative displacement (rotation angle) with respect to the fixed position of the ultrasound probe 1 at the time of generating the volume data 1 to determine the position of the ultrasound probe 1 at the time of generating the volume data 2.

As illustrated in FIG. 11, the body mark generating unit 152c rotates the probe position mark from the initial position in chronological order in accordance with the positional information of the ultrasound probe determined for each item of the volume data newly generated by the extending direction detecting unit 152b.

In this manner, the image synthesizing unit 17 generates a composite image by integrating the display image generated by the display image generating unit 151a and the body mark whose probe position mark is rotated from the initial position, and the monitor 2 displays the composite image based on the control of the control unit 18.

Figure 12:
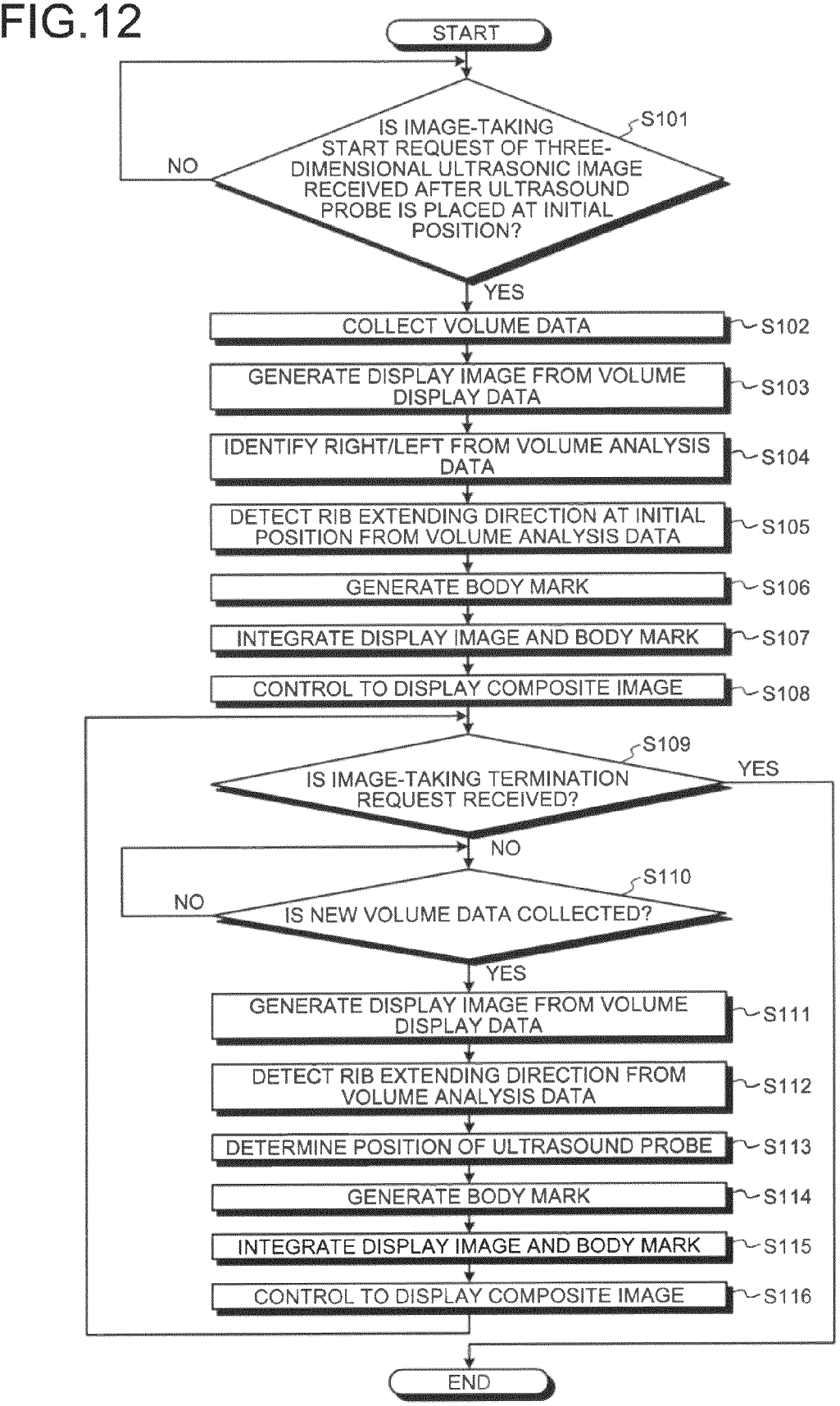
FIG. 12 is a flowchart of the process executed by the ultrasonic diagnostic apparatus according to the present embodiment.

Next, the process executed by the ultrasonic diagnostic apparatus according to the present embodiment is explained with reference to FIG. 12. FIG. 12 is a flowchart for explaining the process executed by the ultrasonic diagnostic apparatus according to the present embodiment.

As illustrated in FIG. 12, when receiving a start request for taking a three-dimensional ultrasonic image after the ultrasound probe 1 is placed at the initial position (yes at step S101), the ultrasonic diagnostic apparatus according to the present embodiment collects volume data (volume analysis data) (step S102). According to the present embodiment, the volume analysis data is collected successively in chronological order, with the ultrasound probe 1 fixed to the initial position until step S108 is completed.

Then, the display image generating unit 151a generates a display image from the volume display data in the volume analysis data (step S103). The display image generating unit 151a successively generates display images for items of the volume display data that are collected in chronological order. The generated display images are synthesized with character information of parameters and scales by the image synthesizing unit 17 and displayed on the monitor 2.

Then, the right/left identifying unit 152a identifies the right or left breast that is being scanned, based on the section images that are successively generated by the analysis image generating unit 151b from the volume analysis data in chronological order (step S104). In other words, the right/left identifying unit 152a calculates the intensity ratio of heartbeat-related cyclic motion components to respiration-related cyclic motion components among the cyclic motion components in the region beneath the ribs of the section images generated in chronological order and thereby identifies the right or left.

Thereafter, the extending direction detecting unit 152b detects the rib extending direction at the initial position according to the first or second method, based on the volume analysis data generated at a certain time when the ultrasound probe 1 is fixed to the initial position (step S105).

Then, the body mark generating unit 152c generates a body mark by integrating the body mark of the right or left breast and the probe position mark indicating the initial position of the ultrasound probe 1, based on the identification result obtained by the right/left identifying unit 152a (step S106).

Thereafter, the image synthesizing unit 17 synthesizes the latest display image generated by the display image generating unit 151a and the body mark generated by the body mark generating unit 152c (step S107). The control unit 18 performs control so that the composite image generated by the image synthesizing unit 17 is displayed on the monitor 2 (step S108).

When checking the monitor 2 to see the probe-position-mark-attached body mark being displayed, the operator judges whether to continue the image-taking by conducting the rotational scanning of the ultrasound probe 1 or terminate the image-taking. When terminating the image-taking, the operator may press the stop button of the input device 3.

When receiving an image-taking termination request from the operator by way of the input device 3 (yes at step S109), the control unit 18 terminates the process.

On the other hand, when an image-taking termination request is not received after step S108 (no at step S109), the control unit 18 judges whether a new item of volume data (volume analysis data) is collected (step S110).

If no new volume data is collected (no at step S110), the ultrasonic diagnostic apparatus is put into standby mode.

On the other hand, when a new item of volume data is collected (yes at step S110), the display image generating unit 151a generates a display image from the volume display data of the new volume analysis data item (step S111), and the extending direction detecting unit 152b detects the rib extending direction from the new volume analysis data item, according to the first or second method (step S112).

Then, the extending direction detecting unit 152b acquires a relative displacement (rotation angle) with respect to the position of the ultrasound probe 1 at the time of generating the previously collected volume data, based on the relative change of the rib extending direction detected at step S112 with respect to the rib extending direction previously detected, and thereby determines the position of the ultrasound probe 1 at the time of generating the new volume data item (step S113). When performing the process at step S113, the extending direction detecting unit 152b determines the position of the ultrasound probe 1 from the relative change of the rib extending direction detected at step S112 with respect to the rib extending direction detected at the initial position at step S105.

The body mark generating unit 152c generates the body mark by integrating the right or left body mark and the probe position mark indicating the current position of the ultrasound probe 1, based on the position of the ultrasound probe 1 determined by the extending direction detecting unit 152b (step S114).

Thereafter, the image synthesizing unit 17 integrates the display image generated by the display image generating unit 151a at step S111 and the body mark generated by the body mark generating unit 152c (step S115), and the control unit 18 performs control so that the composite image generated by the image synthesizing unit 17 is displayed on the monitor 2 (step S116).

Then, the system returns to step S109, where the control unit 18 judges whether an image-taking termination request is received from the operator by way of the input device 3. When the image-taking termination request is not received (no at step S109), the ultrasonic diagnostic apparatus executes the operations of step S110 and the subsequent steps.

According to the present embodiment, the analysis image generating unit 151b generates section images in chronological order from the volume analysis data that is collected by the ultrasound probe 1 transmitting an ultrasound wave down to the region under the ribs in the ultrasonic breast examination. The right/left identifying unit 152a calculates the intensity ratio of the heartbeat-related cyclic motion components to the respiration-related cyclic motion components among the cyclic motion components of the region under the ribs in the chronologically generated section images and thereby identifies the right or left breast that is being scanned.

Then, the extending direction detecting unit 152b performs an edge extracting process on the plane-A images generated by the analysis image generating unit 151b from the same volume analysis data, and thereby detects the rib extending direction (the first method). Alternatively, the extending direction detecting unit 152b analyzes the brightness histograms of different line segments of interest in the plane-C thickness-added MIP images generated from the same volume analysis data by the analysis image generating unit 151b, and thereby detects the rib extending direction (the second method).

Furthermore, the extending direction detecting unit 152b detects the rib extending direction every time the volume analysis data is collected, and thereby determines the position of the ultrasound probe 1 based on the relative displacement of the extending direction and the initial position of the ultrasound probe 1. The body mark generating unit 152c generates a body mark by integrating the right or left body mark determined based on the identification result obtained by the right/left identifying unit 152a and the probe position mark indicating the position of the ultrasound probe 1 determined by the extending direction detecting unit 152b. Then, the image synthesizing unit 17 generates a composite image by integrating the display image generated by the display image generating unit 151a from the volume display data in the observation region of the volume analysis data with the body mark generated by the body mark generating unit 152c, and this composite image is displayed on the monitor 2.

Thus, the operator does not have to manually set the right or left body mark, and identification of the right or left breast that is being scanned and determination of the position of the ultrasound probe 1 can be conducted only with the image processing executed by the ultrasonic diagnostic apparatus to display the body mark together with the probe position mark. Therefore, the positional information of the ultrasound probe at the time of generating an ultrasonic image can be easily obtained, as described above as the main features of the invention.

In addition, the display image from which the region under the ribs is removed is displayed together with the positional information of the ultrasound probe 1 so that the doctor would not be disturbed in the image diagnosis.

Figure 13:
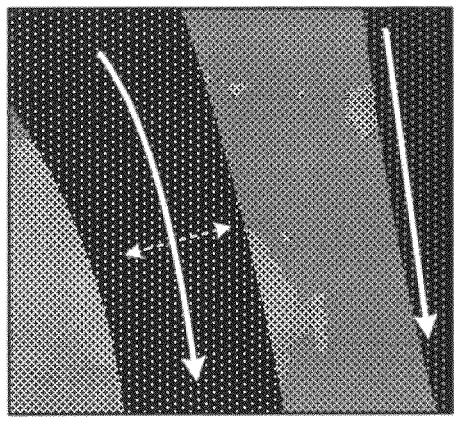
FIG. 13 is a diagram for explaining the first modification example of the present embodiment.
Figure 13:
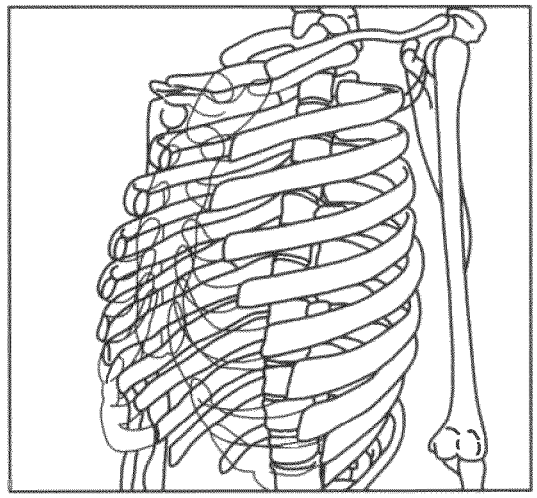
Figure 13:
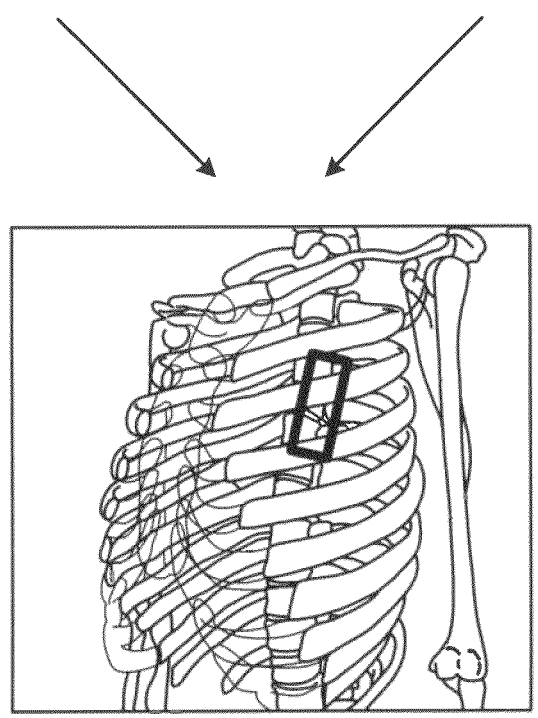

According to the above embodiment, the position of the ultrasound probe 1 is determined based on the initial position of the ultrasound probe 1 and the relative displacement of the rib extending direction, but the present invention is not limited thereto. The position of the ultrasound probe 1 may be determined based on the detected rib extending direction and the anatomical information of the ribs of a healthy body. This technique is now explained with reference to FIG. 13. FIG. 13 is a diagram for explaining the first modification example of the present embodiment.

According to the first modification example, the extending direction detecting unit 152b detects the rib extending direction, the curvature of the rib extending direction, and the distance of the ribs from the plane-C thickness-added MIP image generated by the analysis image generating unit 151b, as illustrated in FIG. 13. Then, the extending direction detecting unit 152b compares the rib extending direction, the curvature of the rib extending direction, and the distance of the ribs with the skeletal information of a healthy body stored in the internal storage unit 19 to determine the position of the ultrasound probe 1, as illustrated in FIG. 13.

In this manner, without setting the initial position of the ultrasound probe 1, the positional information of the ultrasound probe at the time of generating an ultrasonic image can be readily obtained.

Figure 14:
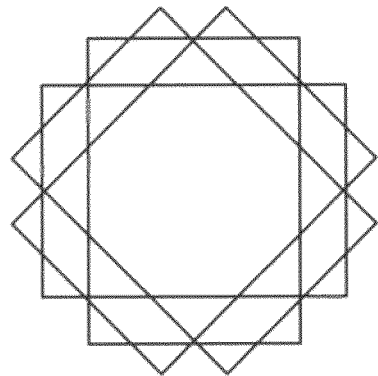
FIG. 14 is a diagram for explaining the second modification example of the present embodiment.

According to the present embodiment, the rib extending direction is used for determination of the position of the ultrasound probe 1, but the present invention is not limited thereto. The rib extending direction may be used for the display of the ultrasonic image. This technique is now explained with reference to FIG. 14. FIG. 14 is a diagram for explaining the second modification example of the present embodiment.

According to the second modification example, the extending direction detecting unit 152b detects the rib extending direction for each item of the volume analysis data to obtain the relative displacement of the rib extending direction. In accordance with the relative displacement of the rib extending direction, the display image generating unit 151a generates a panoramic image by, for example, superimposing the plane-C images generated from different items of the volume display data on one another, as illustrated in FIG. 14.

In this manner, an ultrasonic image that covers all the area in which the ultrasound probe 1 moves is displayed, and thus the effectiveness of the doctor's image diagnosis incorporating ultrasonic images can be improved.

The structural components of the devices illustrated for the above embodiments are to explain the functional concepts, and therefore the devices may not always be physically configured as illustrated. In other words, the separation and integration of the devices is not limited to the illustration in the actual form, and the entire structure or part of the structure may be functionally and physically separated or integrated in any unit in accordance with various loads, usage conditions, and the like.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic diagnostic apparatus, comprising:
    an ultrasonic probe configured to emit an ultrasound wave; and
    processing circuitry configured to
        set a depth of the ultrasound wave emitted from the ultrasound probe to a value deeper than an observation region of a subject and control the ultrasound wave to conduct three-dimensional scanning;
        generate a three-dimensional ultrasonic image based on a reflection wave of the ultrasound wave emitted by the ultrasound probe in accordance with the control and generate a section image orthogonal to scan lines of the ultrasound wave from the three-dimensional ultrasonic image;
        detect through image analysis a rib extending direction depicted in the generated three-dimensional ultrasonic image, acquire a position of the ultrasound probe with respect to the subject based on the detected rib extending direction, and acquire the position that is acquired, as positional information of the ultrasound probe; and
        control display of a mark based on the acquired positional information on a predetermined display, wherein
    the processing circuitry is further configured to detect the rib extending direction based on pixel values of pixels included in the generated section image.

2. The ultrasonic diagnostic apparatus according to claim 1, wherein:
    the processing circuitry is further configured to detect the rib extending direction in a newly generated three-dimensional ultrasonic image in chronological order, and acquire a relative displacement of the ultrasound probe from a relative change of the detected rib extending direction in the three-dimensional ultrasonic image and the detected rib extending direction in the newly generated three-dimensional ultrasonic image; and
    control a movement and display of the mark displayed on the predetermined display based on the relative displacement of the ultrasound probe.

3. The ultrasonic diagnostic apparatus according to claim 1, wherein:
    the processing circuitry is configured to
        determine the position of the ultrasound probe based on the detected rib extending direction and anatomical information of ribs of a healthy human body; and
        control a display of the position of the ultrasound probe on the predetermined display.

4. The ultrasonic diagnostic apparatus according to claim 1, wherein the processing circuitry is configured to control a display of the positional information on the predetermined display together with a generated ultrasonic image based on a reflection wave in the observation region.

5. The ultrasonic diagnostic apparatus according to claim 1, wherein
    the processing circuitry generates a thickness-added maximum intensity projection image in a plane orthogonal to the scan lines of the ultrasound wave as the section image.

6. A positional information acquiring method, comprising:
    performing control to set a depth of an ultrasound wave emitted by an ultrasound probe to a value deeper than an observation region of a subject and to control the ultrasound wave to conduct three-dimensional scanning;
    generating a three-dimensional ultrasonic image, based on a reflection wave of the ultrasound wave emitted by the ultrasound probe and further generating a section image orthogonal to scan lines of the ultrasound wave from the three-dimensional ultrasonic image;
    detecting, by a processing circuit through image analysis, a rib extending direction depicted in the generated three-dimensional ultrasonic image, acquiring a position of the ultrasound probe with respect to the subject based on the rib extending direction that is detected, and acquiring the position that is acquired, as positional information of the ultrasound probe; and
    performing control to display a mark based on the acquired positional information on a predetermined displaying unit, wherein
    the detecting the rib extending direction is based on pixel values of pixels included in the generated section image.

7. A computer program product having a non-transitory computer readable recording medium including a plurality of computer executable instructions for image processing to cause a computer to perform a process comprising:
    performing control to set a depth of an ultrasound wave emitted by an ultrasound probe to a value deeper than an observation region of a subject and to control the ultrasound wave to conduct three-dimensional scanning;
    generating a three-dimensional ultrasonic image based on a reflection wave of the ultrasound wave emitted by the ultrasound probe and further generating a section image orthogonal to scan lines of the ultrasound wave from the three-dimensional ultrasonic image;
    detecting, through image analysis, a rib extending direction depicted in the three-dimensional ultrasonic image generated, acquiring a position of the ultrasound probe with respect to the subject based on the rib extending direction that is detected, and acquiring the position that is acquired, as positional information of the ultrasound probe; and
    performing control to display a mark based on the positional information that is acquired on a predetermined displaying unit, wherein
    the detecting includes detecting the rib extending direction based on pixel values of pixels included in the generated section image.

* * * * *